United States Patent [19]

Farley

[11] Patent Number: 5,025,780
[45] Date of Patent: Jun. 25, 1991

[54] TABLE MOUNTED SURGICAL RETRACTOR

[76] Inventor: Daniel K. Farley, 601 E. Lake Shore Dr., Barrington, Ill. 60010

[21] Appl. No.: 461,816

[22] Filed: Jan. 8, 1990

Related U.S. Application Data

[62] Division of Ser. No. 343,807, Apr. 26, 1989, Pat. No. 4,971,038.

[51] Int. Cl.⁵ ............................................. A61B 17/02
[52] U.S. Cl. ...................................... 128/20; 403/18; 403/389
[58] Field of Search .......................... 128/20; 269/328; 403/87, 93, 110, 112, 18, 389

[56] References Cited

U.S. PATENT DOCUMENTS

| | | | |
|---|---|---|---|
| 1,707,689 | 4/1929 | Sloan | 128/20 |
| 3,221,763 | 12/1965 | Thompson et al. | 128/20 |
| 3,227,156 | 1/1966 | Gauthier | 128/20 |
| 3,384,077 | 5/1968 | Gauthier | 128/20 |
| 3,572,326 | 3/1971 | Jensen | 128/20 |
| 3,810,462 | 5/1974 | Szpur | 128/20 |
| 4,099,521 | 7/1978 | Nestor et al. | 128/20 |
| 4,133,081 | 1/1979 | Hurson | 128/20 |
| 4,143,652 | 3/1979 | Meier et al. | 128/20 |
| 4,337,762 | 7/1982 | Gauthier | 128/20 |
| 4,467,791 | 8/1984 | Cabrera et al. | 128/20 |
| 4,617,916 | 10/1986 | LeVahn et al. | 269/328 |
| 4,718,151 | 1/1988 | LeVahn et al. | 128/20 |
| 4,813,401 | 3/1989 | Grieshaber | 128/20 |
| 4,867,404 | 9/1989 | Harrington et al. | 128/20 |

Primary Examiner—Edward M. Coven
Assistant Examiner—Mark S. Graham
Attorney, Agent, or Firm—McAndrews, Held & Malloy

[57] ABSTRACT

A surgical retractor apparatus for retracting anatomy during surgery includes a single support post connected directly to an adjustable clamp which can be attached to the rail of a surgical operating table. A butterfly assembly positioned on the clamp above the field of sterilization allows operating room personnel to fasten the clamp anywhere along the table rail without breaking the sterile field. Extension arms are connected to the support post by means of adjustable joint clamps. The threaded components of the joint clamps and adjustable clamp may be exposed for easy cleaning and lubrication but may not be completely disassembled thereby facilitating reassembly of the components. Retractor blades are adjustably connected to the extension arms by means of additional joint clamps and extend downwardly through an incision to retract anatomy to provide exposure to the operative site.

16 Claims, 4 Drawing Sheets

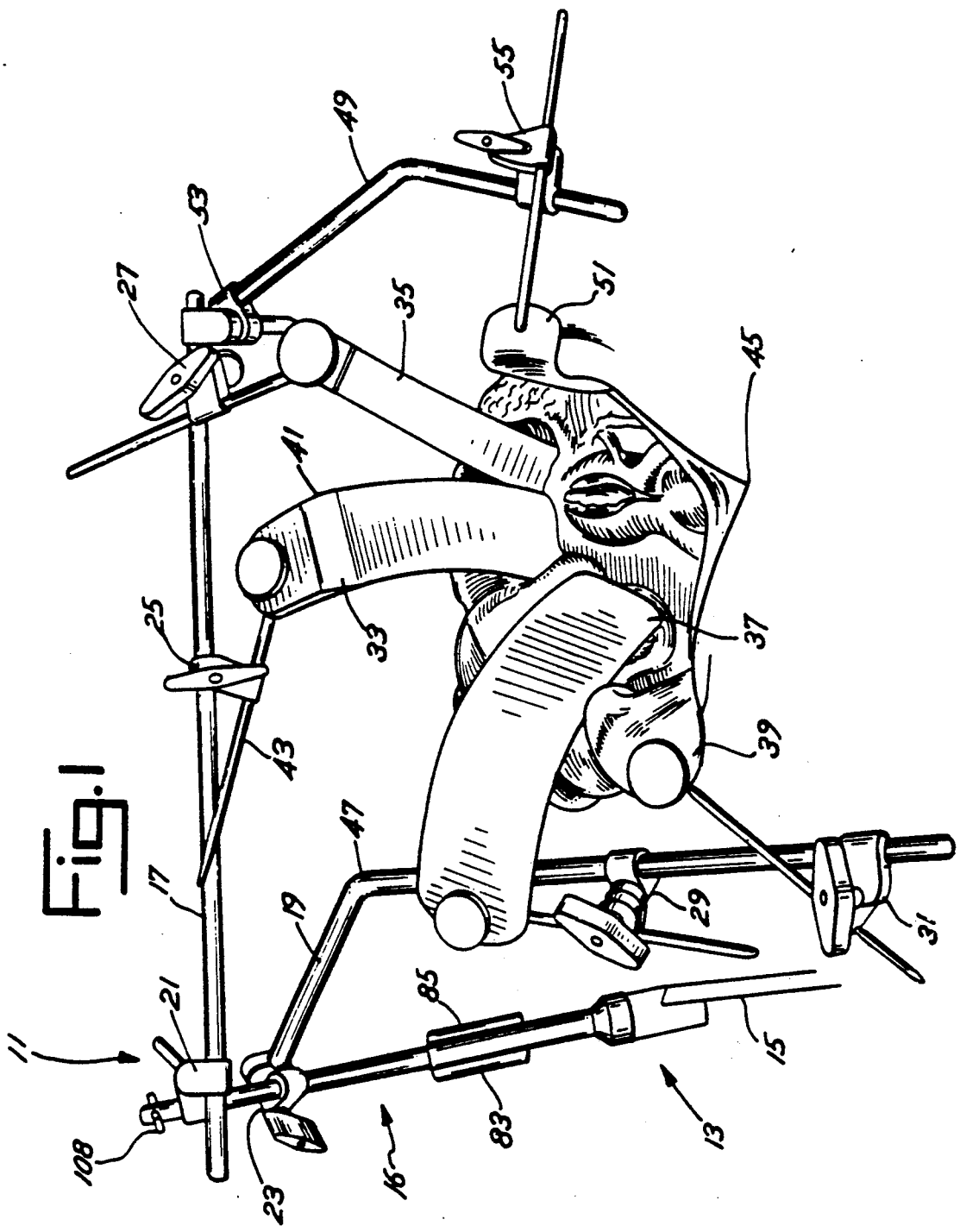

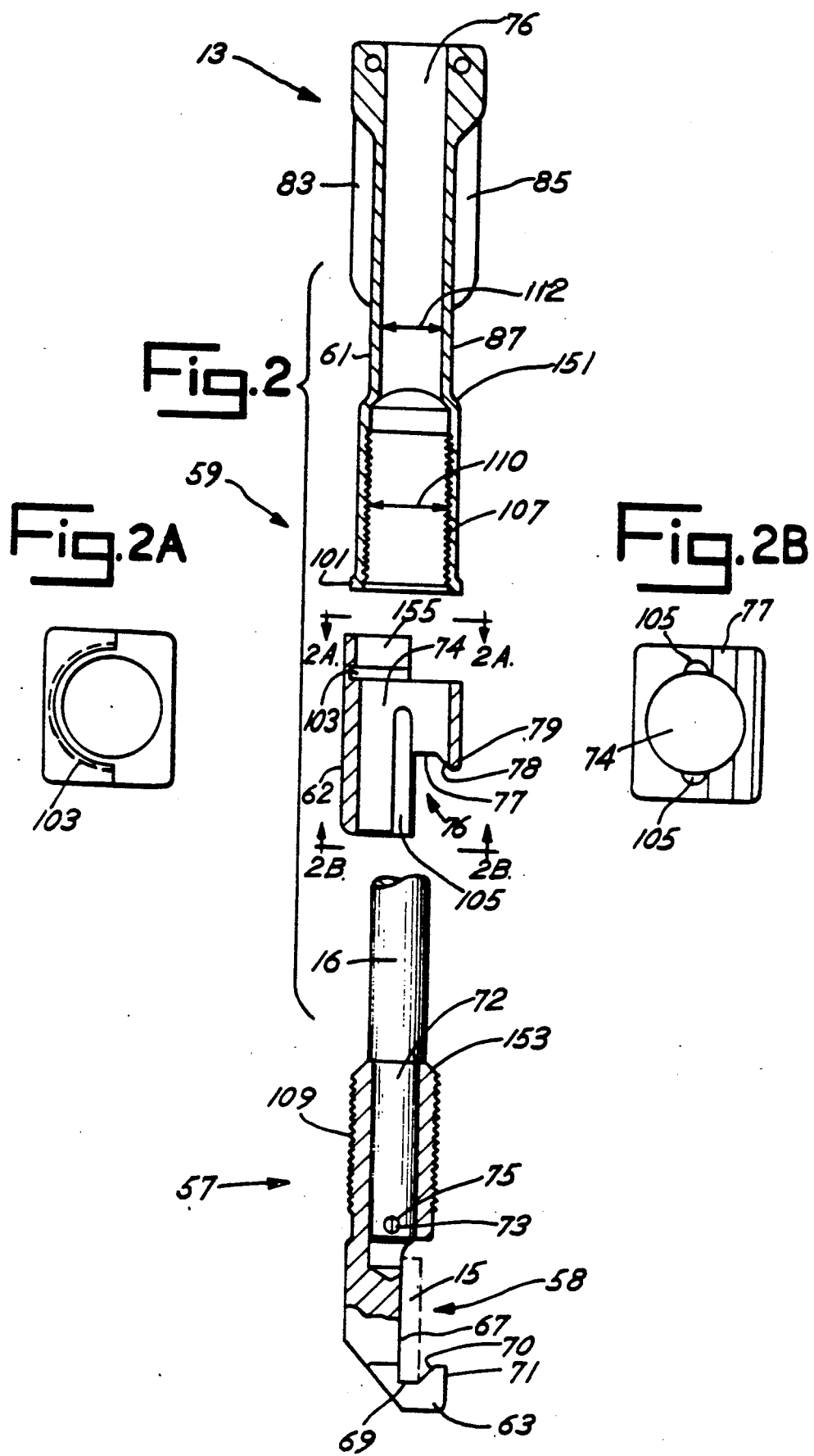

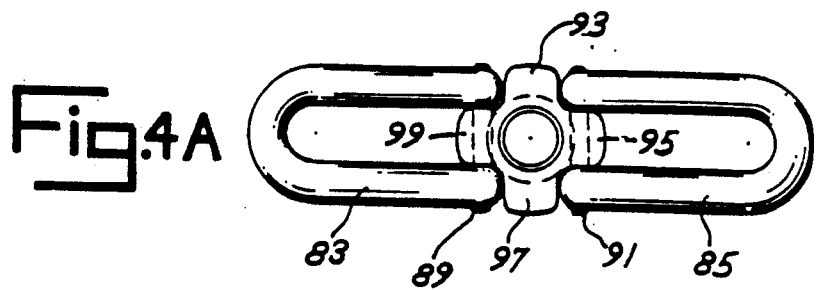
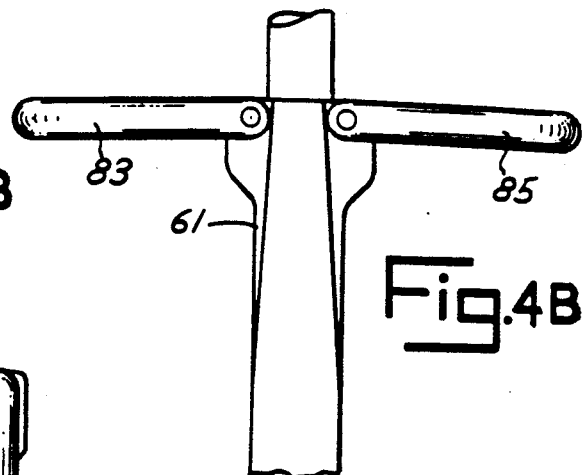
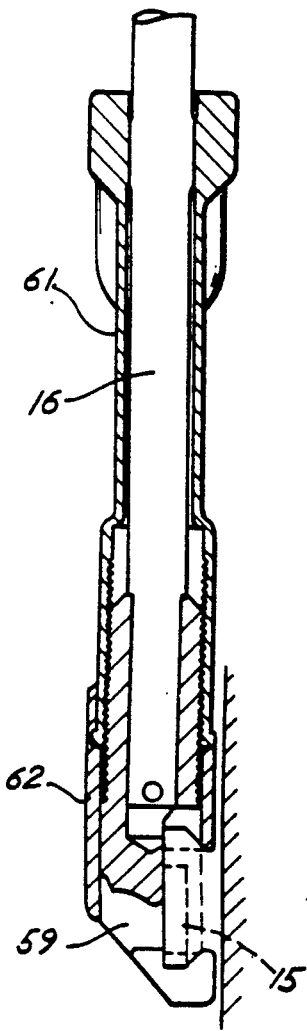
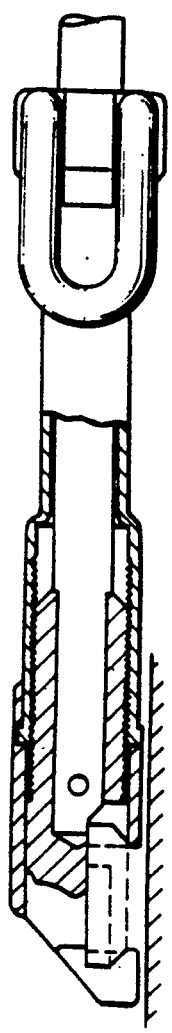
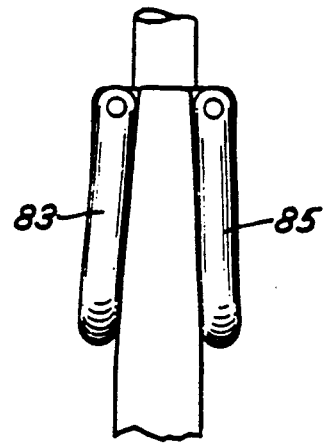

TABLE MOUNTED SURGICAL RETRACTOR

This is a divisional of application Ser. No. 07/343,807, filed Apr. 26, 1989, now U.S. Pat. No. 4,971,038.

BACKGROUND OF THE INVENTION

The invention relates to surgical apparatus for retracting anatomy to provide exposure of the operative site, and more particularly relates to retraction apparatus which is sturdy, adjustable and conducive to thorough sterilization.

In surgical operations, retraction apparatus is needed to access internal organs and bone structures. Variance in types of surgery and patient size necessitates a device which is both adjustable and sturdy. In addition, equipment sterilization requirements call for a device which can be thoroughly cleansed by conventional means in a safe and easy manner.

Heretofore, surgical retraction devices utilize one or two different types of connecting joint mechanisms. The first type of joint consists of several parts which allow the surgeon to swivel and/or rotate the retractor blades into place. Recent trends in the sterilization process require the disassembly of all components of the retractor for autoclaving. As a result, operating room personnel must re-assemble the components of the retractor in surgery. This process is slow and costly. An example of such a device is disclosed in U.S. Pat. No. 4,627,916.

The second type of joint consists of a single part which cannot be disassembled. This joint can be easily sterilized and readied for use in surgery; however, the joint does not offer the surgeon the ability to swivel the retractor blade into place. An example of such a part is disclosed in U.S. Pat. No. 4,254,763.

In addition, table mounted surgical retraction devices utilize rail clamps. The first type of clamp commonly used may not be secured to an operating table without breaking the sterile field. During surgery, repositioning of this rail clamp must be performed by a non-sterile circulating nurse, thereby increasing the duration of the surgery. An example of such a rail clamp is disclosed in U.S. Pat. No. 4,617,916.

The second type of clamp commonly used may be secured to an operating table without breaking the sterile field. However, without disassembly, such clamps do not permit access to internal threads of the clamp for proper cleaning and lubrication. Saline solution and blood not completely removed during the sterilization process will subject the threads to premature galling, marring, and stripping. An example of such a rail clamp is disclosed in U.S. Pat. No. 4,254,763.

It is therefore an object of the present invention to provide an improved surgical retractor.

It is therefore an object of the present invention to provide a surgical retractor having connection joints which facilitate the exact placement of retractor blades relative to the patient as well as facilitate efficient and sufficient cleaning, lubrication, and sterilization.

It is a further object of the present invention to provide a surgical retractor having a rail clamp which may be secured to an operating table without breaking the sterile field and facilitates the cleaning, lubrication, and sterilization of securing threads without disassembling the clamp.

SUMMARY OF THE INVENTION

These and other objects of the invention are achieved in a surgical retraction device which retracts anatomy during all types of surgery. The device includes a rail clamp which can be adjusted in order to fasten the overall retraction system anywhere along a rail provided on a surgical operating table without breaking the sterile field. In one embodiment, the rail clamp is a single unit design which prevents disassembly of its components for easy assembly as well as facilitates exposure of the components for cleaning and lubrication purposes.

In addition, the device includes extension arms which lend support to retractor blades extending downwardly into the operative site. A joint mechanism is used to connect the retractor blades to the extension arms. In one embodiment, the joint mechanism is a single unit design which prevents disassembly of its components for easy assembly as well as facilitates exposure for cleaning and lubrication purposes before assembly.

BRIEF DESCRIPTION OF THE DRAWINGS

FIG. 1 is a perspective view of a surgical retraction system embodiment of the present invention.

FIG. 2 is an exploded cross-sectional view of a single rail clamp and support post of the retraction system of FIG. 1.

FIGS. 2A and 2B are top and bottom views of the upper jaw member of the rail clamp of FIG. 2.

FIGS. 3A and 3B are cross-sectional partial views of the rail clamp of FIG. 2.

FIGS. 4A, 4B, and 4C are top and side views of the handle portion of the rail clamp of FIG. 2.

DETAILED DESCRIPTION OF A PREFERRED EMBODIMENT

Figure 5:
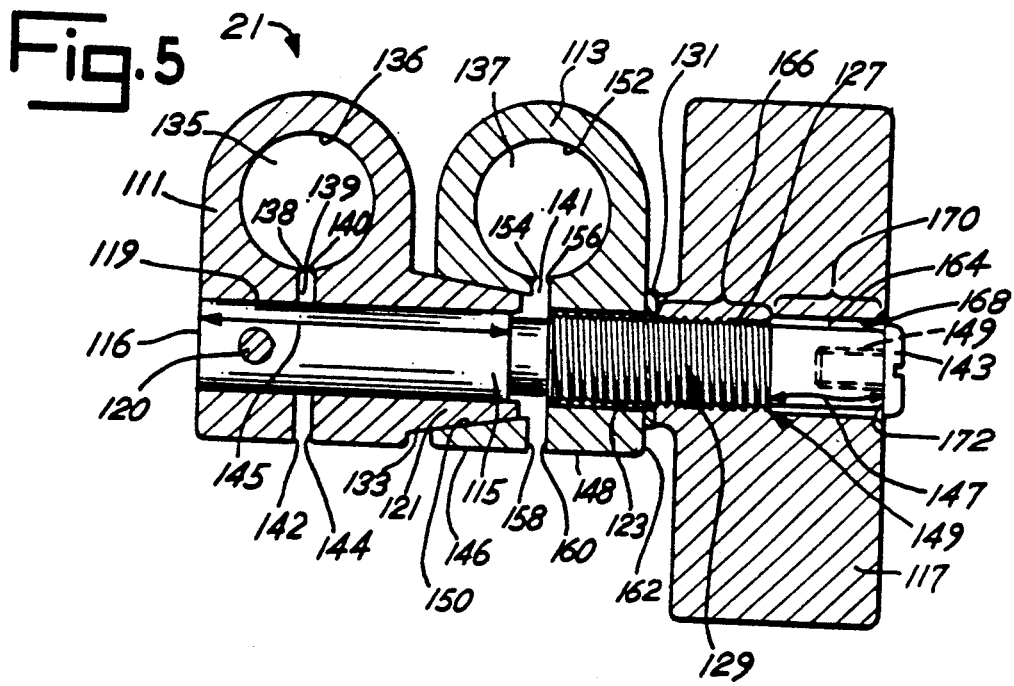
FIGS. 5, 6 and 7 are a cross-sectional side view, a bottom view and an end view respectively of a joint clamp of the retraction system of FIG. 1.

Referring to FIG. 1, a surgical retraction system 11 includes an adjustable rail clamp 13 which is securable to the horizontal rail 15 of a conventional operating table (not shown). A support post 16 extends vertically from rail clamp 13 providing a support for a pair of extension arms 17,19. Arms 17,19 are respectively secured to post 16 by a pair of multi-directional joint clamps 21,23. Additional joint clamps 25,27,29,31 are disposed along arms 17,19 for rigidly securing four separate retractor blades 33,35,37,39 to extension arms 17,19.

Each retractor blade includes a blade portion 41 and a cylindrical rod 43. Blade 41 extends downwardly into the incision 45 made by the surgeon. As understood, the blade portion is used to retract anatomy to make the incised opening accessible to the surgeon.

Extension arm 17 is a cylindrically shaped rod which extends linearly from support post 16. Extension arm 19 is also a cylindrically shaped rod but includes a single bend at 47 intermediate its length. The overall system 11 can be adapted to provide additional retraction by adding components such as an additional extension arm 49 and retractor blade 51. Additional arm 49 is connected to arm 17 by joint clamp 53, and retractor blade 51 is connected to arm 49 by joint clamp 55.

As shown in FIG. 2, rail clamp 13 is formed from a lower jaw 57 and an upper jaw 59. Upper jaw 59 is comprised of two separable components: a jaw drive member 61 and an upper jaw carrying member 62. The three jaw components 57,61,62 are associated with post 16 in order to secure the post to rail 15.

Lower jaw 57 is generally rectangular in shape having a cut away area 58 in one side of jaw 57 for receiving rail 15 (shown in dotted lines). A flat vertical surface 67 is formed in one side of jaw 57 and serves to mate against the flat outer side of rail 15. A lower jaw chin 63 extends fully under rail 15 providing a flat jaw surface 69 which supports the flat underside of rail 15. A lip 71 protrudes outwardly from and above jaw surface 69 providing an angled surface 70 which opposes the back surface of rail 15.

Lower jaw 57 is axially bored in its upper end to form a cylindrical hollowed area 72 which receives the lower end of support post 16. A dowel pin 73 is inserted through lower jaw 57 and through an aperture 75 formed in the lower end of support post 16 so as to fasten support post 16 directly to lower jaw 57. Dowel pin 73 prevents lower jaw 57 from being removed from the lower end of post 16. In addition, support post 16 extends upwardly through a pair of hollowed areas 74,76 formed respectively in jaw carrying member 62 and in jaw drive member 61.

Jaw carrying member 62 is generally rectangular in shape having cylindrical hollowed area 74 disposed along its longitudinal axis. Member 62 has a cut away area 76 for receiving rail 15. A flat jaw surface 77 is formed in jaw member 62 and serves to mate against the flat topside of rail 15. A lip 79 protrudes outwardly from and below jaw surface 77 providing an angled surface 78 which opposes the back surface of rail 15. When positioned as shown in FIGS. 3A and 3B, jaw member 62 maintains contact with the topside of the surgical table rail 15.

Drive member 61 is rotatably mounted to jaw member 62 by an annular flange 101 formed at the lower end of drive member 61. The upper end of jaw member 62 includes a semicircular bored section 155 having a groove 103 of a size to receive annular flange 101. During assembly, flange 101 is laterally moved into groove 103, and thereafter post 16 is passed through hollow areas 74,76 in the upper jaw. Post 16 prevents drive member 61 and jaw member 62 from being detached. This structure prevents vertical separation of jaw carrying member 62 from drive member 61 while permitting rotation of drive member 61 relative to jaw member 62.

A vertical guide slot 105 is formed in both sides of jaw member 62. Slot 105 is keyed to dowel pin 73 which protrudes from the sides of lower jaw 57. As jaw carrying member 62 is driven downwardly to grip the top of rail 15, pin 73 moves upwardly within slot 105. This prevents rotational movement of the jaw carrying member 62 as drive member 61 is rotated.

As shown in FIG. 2, drive member 61 includes a set of internal threads 107 formed within bore area 76. A second set of threads 109 surrounds the upper portion of lower jaw 57. Thread sets 107,109 engage as drive member 61 is manually rotated in a clockwise direction. Rotation of drive member 61 forces both jaw surfaces 69,77 toward one another to grip surgical table rail 15. Drive member 61 is rotated until the two flat jaw surfaces 69,77 securely tighten against rail 15. As shown in FIG. 3, different sizes of rails may be gripped by the two jaws. As shown, it is not necessary that surfaces 69,77 seat directly against the rail in order to secure the rail clamp into position. Instead, angled surfaces 70, 78 may perform the gripping function.

When drive member 61 is manually rotated in a counter clockwise direction, upper jaw 59 recedes from lower jaw 57 relinquishing the grasp on rail 15. Continued counterclockwise rotation of the drive member will cause complete separation of thread sets 107, 109. After thread separation, upper jaw 59 is free to slide along support post 16. A dowel pin 108 (FIG. 1) is positioned through an aperture in the upper end of post 16 for preventing the removal of upper jaw 59 from support post 16.

With the upper jaw 59 disengaged from the lower jaw, thread sets 107,109 become exposed for cleaning. The inner threaded diameter 110 of thread set 107 is larger than the diameter of inserted support post 16 thus allowing ultrasonic cleaning and autoclaving to easily reach thread set 107. Thread set 109 is openly exposed for cleaning and autoclaving.

The diameter 110 of the thread set 107 is larger than the diameter 112 of the upper portion of hollow area 76 above thread set 107. A bottleneck at location 151 contacts an angled periphery surface 153 of lower jaw 57 to control the extent of opposing movement of jaws 57,59. Dowel pin 108 (FIG. 1) and dowel pin 73 serve as a pair of stops which maintain the components as a single-unit structure. The structure, thus, does not need to be disassembled into several components in order to be cleaned, and can be easily manipulated to perform its clamping function.

A pair of manual control handles 83,85 are disposed at the uppermost end of drive member 61. The midsection 87 of the drive member is elongated a sufficient length to extend handles 83,85 above the field of sterilization, generally above waist height in the operating room. This permits the surgeon to operate the rail clamp via handles 83,85 without breaking the field of sterilization.

Referring to FIGS. 4A, 4B and 4C, control handles 83,85 are generally U-shaped and are pivotably fastened to drive member 61 by respective pins 89,91. As shown in FIG. 4A, the top of drive member 61 is formed with four protruding areas 93,95,97,99. Protruding areas 95,99 serve as bearings for pins 89,91.

Figure 6:
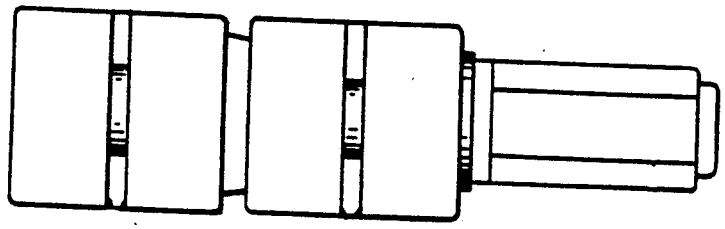
Figure 7:
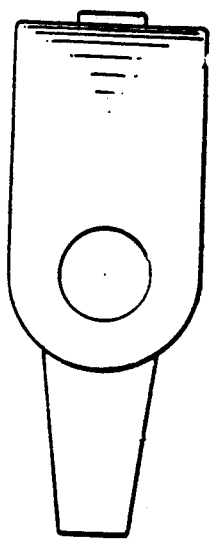

Referring now to FIGS. 5,6 and 7, one clamp 21 of the single joint clamps 21-31,53,55 is shown in more detail. Clamp 21 is formed from two jaw or clamping members 111,113, a partially threaded cylindrical axle or shaft 115, and a securing knob 117. Knob 117 is manually rotated in order to lock clamping members 111,113 relative to shaft 115 as well as to cause a gripping action to take place by each clamping member.

Clamping member 111 includes a cylindrical bore 119 for receiving shaft 115. Shaft 115 is cylindrical in cross section and is permanently fixed in bore 119 by a dowel pin 120. Pin 120 prevents clamping member 111 from being removed from the distal end 116 of shaft 115. As will suggest itself, shaft 115 may be secured to member 111 by other means including welding, rivoting, etc.

Clamping member 111 is integrally formed with a holding section 121 which extends along the axis of bore 119 and surrounds shaft 115. Holding section 121 has a frustumconical outer surface 133 for mating with clamping member 113, as described hereinafter.

In addition, clamping member 111 includes a cylindrical passage 135 which is defined by a broken cylindrical surface 136. Surface 136 is broken along two parallel line edges 138,140 which run the axial length of surface 136 to define a gap 139. Edges 138,140 are moveable with respect to one another in order to shorten gap 139 and thus constrict the area circumscribed by surface 136. Each line edge 138,140 defines a respective planar surface 142,144 each of which pass through bore 119 at approximately 90 degrees. The application of a force against frustumconical surface 133 in a direction parallel to the longitudinal axis of shaft 115 serves to move planar surfaces 142,144 toward each other constricting the area within passage 135.

Clamping member 113 is bifurcated, similar to member 111, having a pair of legs 146,148. Leg 148 includes a cylindrical bore 123 for receiving shaft 115. Leg 146 includes a frustumconical bore 150 for receiving holding section 121. Member 113 is loose about shaft 115 and is moved onto holding section 121 of member 111 by rotation of knob 117. Frustumconical bore 150 slidingly engages frustumconical surface 133 moving to a point on surface 133 until member 113 comes to rest on holding section 121. When member 113 has moved to its full extent resting onto holding section 121, the axis of cylindrical bore 123 is disposed colinear to the axis of shaft 115. At this point, shaft 115 is no longer in contact with clamping member 113 thus preventing frictionally induced stripping of threads 129.

In addition, clamping member 113 includes a cylindrical passage 137 which is defined by a broken cylindrical surface 152. Surface 152 is broken along two parallel line edges 154,156 which run the axial length of surface 152 to define a gap 141. Edges 154,156 are moveable with respect to one another in order to shorten gap 141 and thus constrict the area circumscribed by surface 152. Line edges 154,156 defines a respective planar surface 158,160 which respectively pass through frustumconical bore 150 and bore 123 at approximately 90 degrees. The application of a force by knob 117 against the end surface 162 in a direction parallel to the longitudinal axis of shaft 115 serves to move planar surfaces 158,160 towards each other constricting the area within opening 137.

Knob 117 includes a cylindrical bore 164 for receiving shaft 115. Bore 164 includes a set of threads 127 formed along a section 166 and a flat cylindrical bore surface 168 formed along the remaining section 170. Surface 168 is generally larger in diameter than the inner diameter of threads 127. Threads 127 mate with a set of threads 129 disposed on a portion of shaft 115.

As knob 117 is rotated in a clockwise direction, threads 127,129 guide the knob along shaft 115 towards member 113. A spacing washer 131 is centered about shaft 115 between knob 117 and member 113 and prevents contact therebetween. The clock-wise rotation of knob 117 pushes member 113 towards fixed member 111 until the frustumconical bore 150 becomes seated onto support section 121 of member 111.

At the point at which support section 121 becomes seated within bore 150, further clockwise rotation of knob 117 will force members 111,113 together thereby causing passages 135,137 to constrict. Openings 135,137 are of a size for receiving post 16 or extension arm 17 or the cylindrical rod 43 of retractor 33 (FIG. 1). As a result, members 111,113 firmly grasp the cylindrical arm or rod occupying cylindrical passages 135,137. The clockwise rotation of knob 117 will fix members 111 and 113 in a rotational position relative to the arms passing through their passages.

The threaded portion 129 of shaft 115 is disposed in an area along the shaft which extends into bore 123 of member 113 in order to provide sufficient movement of knob 117 for enabling the constriction of passages 135,137. As will suggest itself, the diameter of the attachment port openings can vary so as to facilitate the joining of cylindrical objects of different diameters.

The counter clockwise rotation of knob 117 will move the knob away from members 111,113 thereby causing the joint clamp to relinquish its grasp on any objects occupying passages 135,137. With further counter clockwise rotation of knob 117, the two sets of threads 127,129 will loose contact with one another thereby allowing knob 117 to freely and rotably slide along the unthreaded portion 147 of shaft 115. The length of unthreaded portion 147 enables thread set 127 to be completely separated from thread set 149.

The removal of knob 117 from the mechanism is stopped by a flathead screw 143 disposed in a threaded bore 149 in the end 172 of shaft 115. The inner diameter of thread set 127 of knob 117 prevents the knob from passing beyond the head of flathead screw 143. Because knob 117 cannot be removed from shaft 115, then neither can spacing washer 131 and member 113.

Dowel pin 120 and flathead screw 143 serve as a pair of stops which maintain the components 111,113,131,117 as a single-unit structure. As a result, joint clamp 21 cannot be taken apart. Therefore, after cleaning, the joint clamp does not require reassembly during surgery. It merely requires the rotation of knob 117.

As will suggest itself, means other than dowel pin 120 and flathead screw 143 can be used to provide stops for joint clamp 21. Also, as will suggest itself, portion 145 of shaft 115 can be axially lengthened so as to accommodate additional rotable holding members similar to members 111, 113 disposed between knob 117 and member 111.

With flathead screw 143 and dowel pin 120 acting as stops, member 113 and spacing washer 131 will be free to rotably slide along the threaded portion 129 of cylindrical shaft 115 disposed between knob 117 and member 111. Holding member 113 comprises frustumconical bore 150 and cylindrical bore 123 which are diametrically larger than the threaded portion of the shaft thereby fully exposing the threads for cleaning and lubrication regardless of the position of the member. In addition, the diameter of the unthreaded portion 147 of shaft 115 is reduced for fully exposing thread set 127 for cleaning and lubrication.

What is claimed is:

1. A universal joint clamp for connecting members of a surgical retraction system relative to one another, said universal joint clamp comprising:
   (i) a shaft member having a first set of threads disposed along a segment of the outer surface of said shaft member;
   (ii) a first clamp member carried by said shaft member and having a first constrictable gripping surface for disposition relative to one of the members of a surgical retraction system for constricting against the one member for securing the one member in a fixed position relative to said first clamp member, and first clamp member including a first contact surface for receiving a force to cause said first constrictable gripping surface to constrict;
   (iii) a second clamp member carried by said shaft member and having a second constrictable gripping surface for disposition relative to another of the members of the surgical retraction system for constricting against the other member for securing the other member in a fixed position relative to said second clamp member, said second clamp member including a second contact surface for receiving a force to cause said second constrictable gripping surface to constrict; said second clamp member rotable and slidable relative to said first clamp member and said second clamp member for applying a force to said first contact surface when said clamp members are forced together;

(iv) knob member having a second set of threads mateable with said first set of threads for causing movement of said knob member along said shaft member, said knob member located distally from said first and second jaw members and being manually rotatable for applying a force to said second contact surface and for forcing said clamp members together to constrict said first and second constrictable surfaces;

(v) first stop member for preventing removal of said first clamp member from one end of said shaft member, said first stop member cooperating with said knob member to fix said clamp members relative to said shaft; and (vi) second stop means for preventing removal of said knob member from the other end of said shaft member, and second stop means being spaced a distance from said segment for permitting said knob member to move to a position which permits cleaning and lubrication of said first and second set of threads.

2. A retraction system according to claim 1 wherein said first clamp member includes a support surface; and wherein said second clamp member includes locating means for cooperating with said support surface for locating said second clamp member relative to said shaft.

3. A retraction system according to claim 2 wherein said support surface and said locating means further cooperate to prevent contact between said second clamp member and said first set of threads when said clamp members are forced together.

4. A retraction system according to claim 2 wherein said support surface is frustumconical in shape.

5. A retraction system according to claim 2 wherein said locating means includes an indentation surface.

6. A retraction system according to claim 5 wherein said indentation surface is of a size to permit access to said first set of threads for cleaning and lubrication.

7. A retraction system according to claim 5 wherein said indentation surface is frustumconical in shape.

8. A retraction system according to claim 1 wherein said first stop means comprise a dowel pin disposed at one end of said shaft member.

9. A retraction system according to claim 8 wherein said dowel pin fixes said first clamp member relative to said shaft member.

10. A retraction system according to claim 1 wherein said second stop means includes a flathead screw driven along the longitudinal axis of said shaft member at said other end thereof.

11. A retraction system according to claim 1 wherein said first contact surface includes a frustumconical surface having an axis colinear with the longitudinal axis of said shaft member.

12. A retraction system according to claim 1 wherein said first constrictable surface is cylindrical in shape having a longitudinal gap defined by a pair of longitudinal edges, said edges being moveable to restrict the volume circumscribed by said first constrictable surface.

13. A retraction system according to claim 12 wherein said pair of edges define a pair of parallel surfaces through which passes said shaft member at an angle of substantially 90 degrees.

14. A retraction system according to claim 1 and further including a washer disposed on said shaft member between said knob member and said second clamp member, said washer contacting said second contact surface to transmit a force supplied by said knob member to said second contact surface.

15. A retraction system according to claim 1 wherein said second clamp member includes a bore through which said first set of threads extends.

16. A retraction system according to claim 15 wherein said bore is of a size to permit access to said first set of threads for cleaning and lubrication.

* * * * *